US007838480B2

(12) United States Patent
Sidwa et al.

(10) Patent No.: US 7,838,480 B2
(45) Date of Patent: Nov. 23, 2010

(54) PROCESS FOR MAKING PERSONAL WASHING BARS EXHIBITING ARTISAN CRAFTED APPEARANCE HAVING SURFACE INCLUSIONS

(75) Inventors: Ewa Urszula Sidwa, New Britain, CT (US); Maria Jose Imbrunito Delben, Valinhos (BR); Cristiane Ayres, Campinas (BR); Mariangela Gomes de Oliveira Sichmann, Campinas (BR); Dikshika Patel, Campinas (BR)

(73) Assignee: Conopco, Inc., Englewood Cliffs, NJ (US)

( * ) Notice: Subject to any disclaimer, the term of this patent is extended or adjusted under 35 U.S.C. 154(b) by 891 days.

(21) Appl. No.: 11/672,095

(22) Filed: Feb. 7, 2007

(65) Prior Publication Data

US 2008/0188388 A1 Aug. 7, 2008

(51) Int. Cl.
*A61K 7/50* (2006.01)

(52) U.S. Cl. ........................ 510/141; 510/151; 510/152; 510/153

(58) Field of Classification Search ........................ None
See application file for complete search history.

(56) References Cited

U.S. PATENT DOCUMENTS

| | | | |
|---|---|---|---|
| 2,296,842 | A | 9/1942 | Garvey et al. |
| 2,520,570 | A | 8/1950 | Short et al. |
| 3,294,692 | A | 12/1966 | Kelly et al. |
| 3,723,325 | A | 3/1973 | Parran, Jr. |
| 4,175,050 | A | 11/1979 | Carduck et al. |
| 4,311,604 | A | 1/1982 | Hornig |
| 4,318,878 | A | 3/1982 | Hornig |
| 5,605,765 | A | 2/1997 | Rudick |
| 6,730,642 | B1 | 5/2004 | Aronson et al. |
| 2003/0171232 | A1 | 9/2003 | Freeman et al. |

FOREIGN PATENT DOCUMENTS

| | | |
|---|---|---|
| DE | 1 617 254 | 11/1967 |
| DE | 41 07 445 A1 | 9/1992 |
| FR | 2 613 724 | 4/1987 |
| GB | 574291 | 12/1945 |
| WO | 99/67355 | 12/1999 |
| WO | 01/46376 A1 | 6/2001 |

*Primary Examiner*—Necholus Ogden, Jr.
(74) *Attorney, Agent, or Firm*—Michael P. Aronson

(57) ABSTRACT

A process is disclosed for the manufacture of a personal washing bar having an artisan crafted appearance that has one or more inclusions emanating from its surface. The process involves forming a billet of an extruded cleansing base; placing one or more inclusion masses on the surface of this billet; and stamping the inclusion bearing billet in a direction perpendicular to the surface on which the inclusion mass is placed so as to embed the inclusion mass in and fuse it with the extruded cleansing base to form a personal washing bar having one or more visually distinct surface inclusions substantially continuous with the continuous phase at the surface of the bar.

11 Claims, 2 Drawing Sheets

PROCESS FOR MAKING PERSONAL WASHING BARS EXHIBITING ARTISAN CRAFTED APPEARANCE HAVING SURFACE INCLUSIONS

FIELD OF THE INVENTION

The invention relates to a process for the manufacture of multiphase personal washing bars that have an artisan crafted appearance suitable for the mass market and to compositions made by this process. Specifically, the process embeds via stamping one or more inclusions masses placed on the surface of a smooth extruded billet of a cleansing base.

BACKGROUND

With the growth of the specialty soap market, consumers are being offered personal washing bars that have a much more hand crafted "one-of a kind" appearance—so called artisan soaps. Technically such bars have several characteristics that contribute to their distinctive appearance: i) sharpness of the boundary between the phases; ii) easily recognizable difference in optical texture and/or pattern that goes beyond color; and iii) a certai degree of bar to bar non-uniformity. Differences in optical texture and pattern are especially important to convey a collection of sensory expectations associated with bar.

To achieve a highly distinctive appearance, artisan soaps have been predominantly made by melt-cast processes—either single casting or sequential multiple casts. For example, U.S. Pat. No. US 2003/0171232-2003 to Freeman et al discloses a decorative soap that contains soap inclusions that are coated with a glitter agent (metallic pigment). The coating makes the soap inclusions resemble a mineral.

Although meltcast processes can yield bars with highly controlled patterns, they are generally slow and labor intensive. Consequently, multiphase artisan soaps are relatively expensive and tend to be confined to upscale specialty shops and outlets. Furthermore, melt-cast soaps are known to have high wear rates and mushing characteristics that make them less preferred for everyday use.

U.S. Pat. No. 6,730,642 to Aronson et al describes an extruded soap into which is dispersed a second phase that is added as solid pieces prior to the final compaction step in billet formation. By controlling the hardness ratio of the two solids, deformation of dispersed phase during extrusion can be minimized thus producing bars with distinctive dispersed inclusions (chunks or bits). Although the process is highly efficient, it has not proved possible to completely eliminate deformation and breakage of the dispersed bits because the composite mass is subject to extensive shear during extrusion.

This deformation during extrusion leads to three problems in connection with fabrication of bars having inclusions. First, the deformation tends to promote the covering of the inclusions by the continuous phase, consequently reducing the number of domains or bits that are distinctly visible at the surface of the freshly made bar.

Secondly, the shear field which deforms the inclusions leads to a "smearing" or "blurring" of the discontinuous domains thus reducing their visual crispness.

Finally, it has so far proved very difficult by previous extrusion processes to control the orientation of the inclusions which tend to be distributed in various orientations within the bar. This problem is especially acute for shaped inclusions designed to have a recognizable shape that would be evident to consumers by cursory visual inspection of the bar, e.g., a flower petal.

Similar problems are encountered with various other processes disclosed in the art to make striped, marbled or variegated soaps wherein multiple phases are combined and subjected to extrusion.

Several publications have addressed this problem. These include:

DE 41 07 445 A1 to Gartner discloses forming a cavity in a body of soap that extends from its surface to its core region and then placing a secondary soap in this cavity.

WO 99/67355 to Fischer discloses a process for the production of multicolored soap involving the insertion of one soap mass into another soap mass of a different color or pattern.

Both U.S. Pat. Nos. 4,318,878 and 4,311,604 to Hornig disclose a soap comprising a primary soap bar body having a cavity designed to receive a secondary soap that is embedded into this cavity.

GB 574, 291 to Slack discloses a soap having a cameo or other artistic feature made by first stamping a white soap with a projection die that creates a recess in the soap. This recess is filled with a second soap and stamped to create the desired relief.

U.S. Pat. No. 4,175,050 to Charduck et al discloses shaped washing agents having a mosaic-like structure made by molding under pressure a mixture of individual colored particles of soap 1-20 mm in size under conditions which remove any occluded gas.

U.S. Pat. No. 3,294,692 to Kelly et al discloses a striped soap bar wherein the bars is made by inserting multiple grooves of differently colored soap utilizing a specially constructed slotted die.

U.S. Pat. No. 5,605,765 to Rudick discloses a decorative composite formed by extruding a plurality of colored rods into a elongated block and then cutting cross-sections that expose the pattern.

DE 1,617,254 to kappus describes a soap bar with strips inlaid in at least one surface wherein a soap pellet is produced with a recess corresponding to the shape of the inclusions (strips) to be inlaid. The inclusions are inserted into this recess starting from the surfaces. The pellets are then cut into tablets and pressed in a form that provides different degrees of compression in different of the form.

The above processes introduce considerable complexity to a conventional soap finishing line in terms of process steps and equipment. Furthermore, they provide only limited flexibility in accommodating different shaped inclusions on the same process line and rapid changeover. Thus, there remains a need for an efficient and flexible high speed processes to make multiphase cleansing bars suitable for mass market that have visually distinctive domains with sharply defined boundaries, which are clearly visible at the surface of the bar, and which can be orientated in a preferred direction.

SUMMARY OF INVENTION

The invention encompasses a process for the manufacture of a multiphase cleansing bar that has surface inclusions which are easily visible domains that have well defined boundaries and shapes. Specifically, the process includes the steps of:

i) forming a billet having a continuous and smooth surface comprised of an extruded cleansing base, ii) placing one or more inclusion masses on the continuous and smooth surface of the billet so as to form an inclusion bearing billet, iii) stamping the inclusion bearing billet in a direction perpendicular to the surface on which the inclusion mass is placed so as to embed the inclusion mass or masses into a surface layer of the billet so as to form a personal washing bar having one or more visually distinct surface inclusions substantially continuous with the continuous phase at the surface of the bar, wherein the extruded cleansing base has a hardness as measured by the Cylinder Impaction Test of at least 20 lb/in$^2$ (1 lb./in$^2$ equals 6.894 kilopascals in SI units) when measured at a temperature in the range of from about 30° C. to about 42° C., preferably a hardness of at least 28 lb/in$^2$ when measured at a temperature in the range from about 33° C. to about 42° C.

In another embodiment of the instant process, steps are included which promote adhesion of the inclusion mass to the surface of the billet before stamping so that the billet can be rotated without the inclusion mass being dislodged.

Another embodiment of the invention is a multiphase bar having surface inclusions wherein the bar comprises:

i) at least 60% of a continuous phase comprised of an extruded cleansing base, ii) up to 30% of a water soluble or water dispersible thermoplastic mass present as visually distinct surface inclusions wherein the surface area of the inclusion visible at the surface of the bar is at least 60% of the maximum cross sectional area of the inclusion in any plane parallel to the surface of the bar, wherein the ratio of the hardness of the of the continuous phase and the hardness of the thermoplastic mass present as surface inclusions is at least about 1.0, preferably at least 1.1, wherein the hardness of the continuous and thermoplastic masses is measured by the Cylinder Impaction Test at the same temperature, said temperature falling within the range of about 30° C. to 42° C.

In a further embodiment of the bar described above, the ratio of the intrinsic wear rate of the inclusion mass and the continuous phase is in the range from about 0.9/1.2 to about 1.2/0.9 wherein the intrinsic wear rate is measured in the Controlled Rubbing Test.

These and other embodiments are described more fully below in the detailed description which should be read in conjunction with the accompanying drawings.

DETAILED DESCRIPTION OF INVENTION

Figure 1:
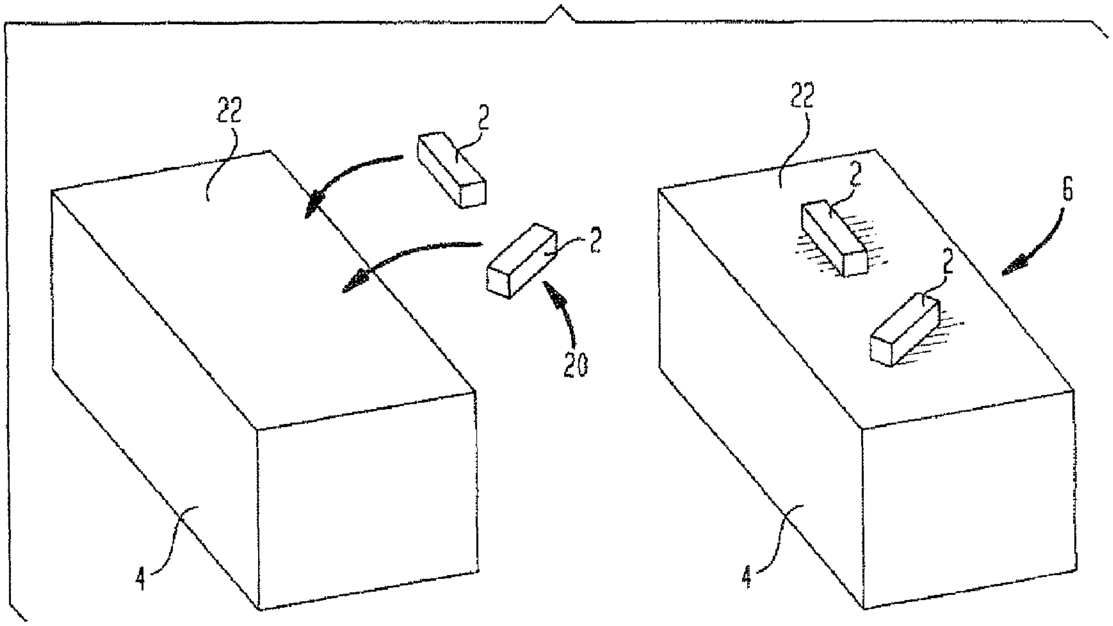
FIG. 1. Perspective view illustrating the placement of inclusion mass on the surface of the continues phase billet prior to stamping.

As used herein % or wt % refers to percent by weight of an ingredient as compared to the total weight of the composition or component that is being discussed.

Except in the operating and comparative examples, or where otherwise explicitly indicated, all numbers in this description indicating amounts of material or conditions of reaction, physical properties of materials and/or use are to be understood as modified by the word "about." All amounts are by weight of the final composition or phase being discussed, unless otherwise specified.

It should be noted that in specifying any range of concentration, any particular upper concentration can be associated with any particular lower concentration.

For the avoidance of doubt the word "comprising" is intended to mean "including" but not necessarily "consisting of" or "composed of." In other words, the listed steps, options, or alternatives need not be exhaustive.

The present invention relates to a process for the production of a multiphase soap having a continuous extruded, phase of an extruded cleansing base and surface inclusions of a thermoplastic mass, designated the "inclusion mass" or "inclusion phase". The process involves two key steps: placement of the inclusion mass on a smooth and continuous surface of a billet comprised of the cleansing base; and directly stamping the inclusion bearing billet to form the finished personal washing bar incorporating surface inclusions.

The nature of the continuous phase and inclusion mass, and the key process steps are described below.

Continuous Extruded Phase

The continuous extruded phase, hereafter also designated simply as the "continuous phase" comprises a cleansing base suitable for cleaning the skin. The cleansing bases comprises from about 25% to about 95% by weight of surfactants, preferably from about 50% to about 90% by weight and most preferably from about 60% to about 85% by weight based on the total weight of the continuous phase.

The surfactants should be suitable for routine contact with human skin and preferably be high lathering. A variety of surfactants can be employed such as those described in U.S. Pat. No. 6,730,642 to Aronson et al incorporated by reference herein.

One especially useful class of surfactants comprises fatty acid soaps. The term "soap" is used herein in its popular sense, i.e., the alkali metal or alkanol ammonium salts of aliphatic, alkane-, or alkene monocarboxylic acids. Sodium, potassium, magnesium, mono-, di- and tri-ethanol ammonium cations, or combinations thereof, are suitable for purposes of this invention. In general, sodium soaps are used in the compositions of this invention, but from about 1% to about 25% of the soap may be potassium, magnesium or triethanolamine soaps. The soaps useful herein are the well known alkali metal salts of natural of synthetic aliphatic (alkanoic or alkenoic) acids having about 8 to 22 carbon atoms, preferably about 10 to about 18 carbon atoms. They may be described as alkali metal carboxylates of saturated or unsaturated hydrocarbons having about 8 to about 22 carbon atoms.

Soaps having the fatty acid distribution of coconut oil may provide the lower end of the broad molecular weight range. Those soaps having the fatty acid distribution of peanut or rapeseed oil, or their hydrogenated derivatives, may provide the upper end of the broad molecular weight range.

It is preferred to use soaps having the fatty acid distribution of coconut oil or tallow, or mixtures thereof, since these are among the more readily available fats. The proportion of fatty acids having at least 12 carbon atoms in coconut oil soap is about 85%. This proportion will be greater when mixtures of coconut oil and fats such as tallow, palm oil, or non-tropical nut oils or fats are used, wherein the principle chain lengths are C16 and higher. Preferred soap for use in the compositions of this invention has at least about 85% fatty acids having about 12 to 18 carbon atoms.

Coconut oil employed for the soap may be substituted in whole or in part by other "high-lauric" oils, that is, oils or fats wherein at least 50% of the total fatty acids are composed of lauric or myristic acids and mixtures thereof. These oils are generally exemplified by the tropical nut oils of the coconut oil class. For instance, they include: palm kernel oil, babassu oil, ouricuri oil, tucum oil, cohune nut oil, murumuru oil, jaboty kernel oil, khakan kernel oil, dika nut oil, and ucuhuba butter.

A preferred soap is a mixture of about 15% to about 40% soaps derived from coconut oil or other lauric rich oils and about 85% to about 60% soaps derived from tallow or other stearic rich oils.

The soaps may contain unsaturation in accordance with commercially acceptable standards. Excessive unsaturation is normally avoided.

Soaps may be made by the classic kettle boiling process or modern continuous soap manufacturing processes wherein natural fats and oils such as tallow or coconut oil or their equivalents are saponified with an alkali metal hydroxide using procedures well known to those skilled in the art. Alternatively, the soaps may be made by neutralizing fatty acids, such as lauric (C12), myristic (C14), palmitic (C16), or stearic (C18) acids with an alkali metal hydroxide or carbonate.

A second broad type surfactant useful in the practice of this invention comprises non-soap synthetic type detergents—so called syndets. Syndets can include anionic surfactants, nonionic surfactants amphoteric or zwitterionic surfactants and cationic surfactants.

The anionic surfactant may be, for example, an aliphatic sulfonate, such as a primary alkane (e.g., $C_8$-$C_{22}$) sulfonate, primary alkane (e.g., $C_8$-$C_{22}$) disulfonate, $C_8$-$C_{22}$ alkene sulfonate, $C_8$-$C_{22}$ hydroxyalkane sulfonate or alkyl glyceryl ether sulfonate (AGS); or an aromatic sulfonate such as alkyl benzene sulfonate.

The anionic may also be an alkyl sulfate (e.g., $C_{12}$-$C_{1-8}$ alkyl sulfate) or alkyl ether sulfate (including alkyl glyceryl ether sulfates).

The anionic surfactant can also be a sulfonated fatty acid such as alpha sulfonated tallow fatty acid, a sulfonated fatty acid ester such as alpha sulfonated methyl tallowate or mixtures thereof.

The anionic surfactant may also be alkyl sulfosuccinates (including mono- and dialkyl, e.g., $C_6$-$C_{22}$ sulfosuccinates), alkyl and acyl taurates, alkyl and acyl sarcosinates, sulfoacetates, $C_8$-$C_{22}$ alkyl phosphates and phosphates, alkyl phosphate esters and alkoxyl alkyl phosphate esters, acyl lactates, $C_8$-$C_{22}$ monoalkyl or alkyl ethoxy succinates and maleates, sulphoacetates, and acyl isethionates.

Another class of anionics is $C_8$ to $C_{20}$ alkyl ethoxy (1-20 EO) carboxylates.

Another suitable anionic surfactant is $C_8$-$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms. The acyl isethionate may also be alkoxylated isethionates Acyl isethionates, when present, will generally range from about 0.5 to about 50% by weight of the total composition. Preferably, this component is present from about 1 to about 15% and most preferably from about 1% to about 10% by weight.

In general the anionic component will comprise from about 1 to 20% by weight of the syndet surfactant base, preferably 2 to 15%, most preferably 5 to 12% by weight of the composition.

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. Suitable amphoteric surfactants include amphoacetates, alkyl and alkyl amido betaines, and alkyl and alkyl amido sulphobetaines.

Amphoacetates and diamphoacetates are also intended to be covered in possible zwitterionic and/or amphoteric compounds which may be used.

The amphoteric/zwitterionic surfactant, when used, generally comprises 0% to 25%, preferably 0.1 to 20% by weight, more preferably 1% to 10% of the surfactant base.

Suitable nonionic surfactants include the reaction products of compounds having a hydrophobic group and a reactive hydrogen atom, for example aliphatic alcohols or fatty acids, with alkylene oxides, especially ethylene oxide either alone or with propylene oxide. Examples include the condensation products of aliphatic ($C_8$-$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar based surfactant, such as a alkyl polysaccharides and alkyl polysaccharide amides.

Examples of cationic detergents are the quaternary ammonium compounds such as alkyldimethylammonium halogenides.

Other surfactants which may be used are described in U.S. Pat. No. 3,723,325 to Parran Jr. and "Surface Active Agents and Detergents" (Vol. I & II) by Schwartz, Perry & Berch, both of which is also incorporated into the subject application by reference.

Although the surfactants comprising the continuous phase may be entirely soap or syndet it is in some cases preferable to uses a combination of soaps with synthetic surfactants. Examples of combination bases are disclosed in U.S. Pat. No. 4,695,395 to Caswell, et al incorporated by reference herein.

In addition to surfactants, the continuous phase can contain various optional ingredients including plasticizing agents, hardening agents, fillers, various adjuvants, and agents that provide skin care benefits. These are described below under OPTIONAL INGREDIENTS.

Regardless of which surfactants are used, the continuous phase is an extruded phase, i.e., must be capable of being made by extrusion. Thus, the continuous phase must posses certain physico-chemical properties that allow it to be mixed and blended in conventional mills, refiners and plodders used in soap production. First, the mass comprising the continuous phase must be thermoplastic within the process temperature of extrusion which is generally at a temperature between about 30° C. and about 42° C., preferably at a temperature between about 33° C. to about 42° C. Thus, the material must soften within this process temperature window but remain highly viscous, i.e., not melt to a low viscosity liquid. The material should also harden quickly as the temperature is lowered below its softening point.

Secondly, the softened mass although pliable must be sufficiently viscous so that is does not stick to the surfaces of the extruder in order to be capable of conveyance by the extruder screws but not bend excessively when exiting the extruder as a billet. However, if the mass is too viscous it will not be capable of extrusion at reasonable rates. Thus, the hardness of the mass should fall within limits within the process temperature window to be capable of high rates of production. By high rate of production is meant in excess of about 50 tablet or bars per minute (4.5 Kg/min for a 90 Kg bar), preferably greater than about 150 bars per minute (13.5 Kg/min), and more preferably greater than 250 bars per minute (22.5 Kg/min.

It has been found experimentally that to achieve the desired rates of production the hardness of the continuous phase mass should be at least about 20 $lbs/in^2$, but not greater than 50 $lbs/in^2$, preferably greater than 26 $lbs/in^2$, and more preferably at least about 28 $lbs/in^2$ as measured by the Cylinder Impaction Test as described in the TEST METHODOLOGY section when carried at temperatures in the range of about 30° C. to about 42° C.

Based on the above hardness criteria, so called melt and pour compositions such as those used to make glycerin soaps that require casting in molds in order to form bars are not suitable as the mass comprising the continuous phase. These compositions are free flowing viscous liquids that can not be extruded.

In addition to the requirement of being extrudable, the continuous phase must also be sufficiently hard to be stamped with conventional soap making dyes (see below). Experience has shown that stamping can be achieved by ensuring that the mass comprising the continuous phase has a minimum hardness of at least 20 $lbs/in^2$ at the stamping temperature which is typically in the range 25° C. to 40° C.

It should be further noted that the continuous phase need not be a single homogeneous phase of a single composition. For example, the continuous phase can contain discrete domains such as those described in U.S. Pat. No. 6,730,642 to Aronson et al, visible particles such as beads and microspheres. The continuous phase can also include stripes or variegations.

The continuous phase can also be composed of two or more coextruded streams of the different compositions. For example a bar comprised of two adjacent coextruded continuous phase containing surface inclusions on one or more faces is within the scope of the invention.

Inclusion Mass

The second mass comprising bars of the invention is the mass that makes up the surface inclusions. The inclusion mass is also a thermoplastic composition in the sense defined above in connection with the continuous phase. In addition, this thermoplastic composition should be water soluble or water dispersible in order to wear away during use as well as contribute to the cleansing and sensory properties of the bar.

The inclusion mass preferably contains one or more surfactants similar to or the same as those used in the continuous phase and discussed above. Preferred surfactants include fatty acid soaps, synthetic surfactants, and a combination of these two types of surfactants. The types and amounts of surfactants in the continuous phase and the inclusion mass can be the same or different. It is preferable that the inclusion mass contains one or more surfactants at a level of at least about 25% by weight of the inclusion mass, more preferably at least about 40% and most preferably at least about 50% by weight of the inclusion mass.

The inclusion mass can also include non surfactant materials provided they yield thermoplastic solids. These non-surfactant materials can be water soluble, water dispersible or water insoluble materials provided the inclusion mass as a whole is water soluble or water dispersible. Examples include polyalkylene glycols such as polyethylene oxide, polypropylene oxides or their copolymers; branched or unbranched wax alcohols or alkoxylates such as self dispersible waxes; polyesters, and other thermoplastic polymers.

Polyalkylene glycol having a melting point above 30° C. is suitable. Preferably, the polyalkylene glycol should have a molecular weight greater than about 4,000 to about 100,000, preferably about 4,000 to about 20,000, most preferably about 4,000 to about 10,000. Minimum MW of about 4,000 is believed to be required so that the inclusion mass is solid at room temperature. A suitable polyalkylene glycol is polyethylene glycol, for example Carbowax® PEG 8000.

Hydrophobically modified polyalkylene glycol (HMPAG) having broad molecular weight 4,000 to 25,000, preferably 4,000 to 15,000 can also be employed. Generally, the polymers will be selected from polyalkylene glycols chemically and terminally attached by hydrophobic moieties, wherein the hydrophobic moiety can be derivatives of linear or branched alkyl, aryl, alkylaryl, alkylene, acyl (e.g., preferably $C_8$ to $C_{40}$; fat and oil derivatives of alkylglyceryl, glyceryl, sorbitol, lanolin oil, coconut oil, jojoba oil, castor oil, almond oil, peanut oil, wheat germ oil, rice bran oil, linseed oil, apricot pits oil, walnuts, palm nuts, pistachio nuts, sesame seeds, rapeseed, cade oil, corn oil, peach pit oil, poppy seed oil, pine oil, soybean oil, avocado oil, sunflower seed oil, hazelnut oil, olive oil, grape seed oil, and safflower oil, Shea butter, babassu oil, etc. The total content of the hydrophobic moiety is preferably 3% wt. to 15% wt. per mole of the defined HMPAG.

Fatty acids, fatty acid esters, and fatty alcohols can be incorporated as part of the inclusion mass. Generally, the fatty group has a chain length between 12 and 22 carbon atoms. Particularly suitable fatty acid ester is glycerol monolaurate.

Still other useful non-surfactant materials are derived from polysaccharides especially starch. These include unmodified starch; starch modified to alter its water solubility, dispersability, and swelling, and hydrolyzed starch such as maltodextran.

In one embodiment the inclusion mass is translucent or transparent provided it has the properties defined above that allow the mass to be extruded. The term "translucency" is typically determined in the art by noting the point size of Roman type letters that can be read clearly through a parallel-faced slice of soap 3 millimeters thick (see for example F. V. Wells, Transparent Soap, Soap and Chemical Specialties, June 1955). The method to quantify translucency used in the present work is the Soap Transparency Test described below in the TEST METHODOLOGY section.

For the reasons discussed below in connection with the preferred process used to make the bars of the invention, it is desirable in one embodiment that the inclusion mass be harder (less pliable) than the continuous phase at the average temperature of the two masses (phases) when the bar is stamped. This average temperature of the continuous phase at stamping is generally within the range of from about 25° C. to about 42° C.

Thus, in this embodiment the inclusion mass should have a penetrometer hardness that is greater than the penetrometer hardness of the continuous phase when measured by the Cylinder Impaction Test at the same temperature.

Preferably the ratio of the penetrometer hardness of inclusion mass to the hardness of the continuous phase measured at the average temperature of the two masses (a mass-weighted average temperature) when they are stamped should be at least about 1.0, preferably at least 1.1, more preferably at least about 1.15, and most preferably at least about a 1.2 when measured by the Cylinder Impaction Test.

In a preferred embodiment, the surface inclusion should wear away during the use of the bar at roughly the same rate as the continuous phase. This can be ensured by selecting the composition of the phases such that the intrinsic wear rates as measured by the Controlled Wear Test set forth in the TEST METHODOLOGY section below are within about 20% of each other, preferably within about 15% of each other and most preferably within about 10% of each other.

It is preferable that the ratio of the intrinsic wear rate of the inclusion mass to the intrinsic wear rate of the continuous phase mass is in the range from about 0.8/1 to about 1.2/1, more preferably about 0.85/1 to about 1.15/1 and most preferably from about 0.9/1 to about 1.1/1.

In contrast in another but less preferred embodiment of the invention the surface inclusions can also serve as massaging elements that can provide a pleasant sensory experience during use. In this case it is desirable that the intrinsic wear rate of the inclusion mass is lower than the intrinsic wear rate of the continuous phase by at least 15%, preferably at least about 20% and more preferably at least about 30%.

Optional Ingredients

Plasticizing Agents

Plasticizing agents are useful components for inclusion in one or both of the continuous and inclusion phase. Here a plasticizing agent is defined as a material that alter the hardness or consistency of the continuous phase, especially at temperatures at which the multiphase bar is stamped. Without being bound by theory, these materials are thought to facilitate stronger bonding between the phases and provide greater resistance against cracking or fracture during use.

A variety of materials can be used as a plasticizer: the key property is that they alter the hardness of the mass or masses at the required temperature.

Oils are particularly useful plasticizers. One useful class of oils is ester oils: oils having at least one ester group in the molecule, especially fatty acid mono and polyesters such as cetyl octanoate, octyl isonanoanate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate; sucrose ester, sorbitol ester, and mixtures thereof.

Triglycerides and modified triglycerides are particularly useful ester oils. These include vegetable oils such as jojoba, soybean, canola, sunflower, palm, safflower, rice bran, avocado, almond, olive, sesame, persic, castor, coconut, and mink oils. These oils can also be hardened to remove unsaturation and alter their melting points. Synthetic triglycerides can also be. Some modified triglycerides include materials such as ethoxylated and maleated triglyceride derivatives. Proprietary ester blends such as those sold by Finetex as Finsolv® are also suitable, as is ethylhexanoic acid glycerides.

Another type of useful ester oil is liquid polyester formed from the reaction of a dicarboxylic acid and a diol. An example of polyesters suitable for the present invention is the polyesters marketed by ExxonMobil under the trade name PURESYN ESTER®.

A second class of oils suitable plasticizing agent is hydrocarbon oil, which includes linear and branched oils such as liquid paraffin, squalene, squalane, mineral oil, low viscosity synthetic hydrocarbons such as polyalphaolefin sold by ExxonMobil under the trade name of PureSyn PAO® and polybutene sold under the trade name PANALANE® or INDOPOL®. Highly branched hydrocarbon oils may also be suitable. Although more properly classified as a grease, petrolatum can also serve as a useful plasticizer.

Some natural and synthetic waxes can also be used as plasticers providing they have the correct melting point and solubility properties.

A third type of material that can function as a plasticizer are C8-C22 fatty acids, preferably C12-C18, preferably saturated, straight-chain fatty acids. However, some unsaturated fatty acids can also be employed. Of course the free fatty acids can be mixtures of shorter (e.g., C10-C14) and longer (e.g., C16-C18) chain fatty acids although it is preferred that longer chain fatty acids predominate over the shorter chain fatty acids.

The fatty acid can be incorporated directly or be generated in-situ by the addition of protic acid. Examples of suitable protic acids include: HCL, adipic acid, citric acid, glycolic acid, acetic acid, formic acid, fumaric acid, lactic acid, malic acid, maleic acid, succinic acid, tartaric acid and polyacrylic acid. Other protic acids are mineral acids such as hydrochloric acids, phosphoric acid, sulfuric acid and the like.

Nonionic surfactants can also serve as plasticizers for the continuous phase. Nonionic surfactants in the context of the instant invention are amphiphilic materials in which the polar groups are uncharged. Examples of suitable nonionic surfactants include: ethoxylates (6-25 moles ethylene oxide) of long chain (12-22 carbon atoms) fatty alcohol (ether ethoxylates) and fatty acids; alkyl polyhydroxy amides such as alkyl glucamides; alkyl polyglycosides; esters of fatty acids with polyhydroxy compounds such as glycerol and sorbitol; ethoxylated mono-, di- and triglycerides, especially those that have lower melting points; and fatty amides.

Organic bases, especially alkoxy amines like triethanolamine are also useful plasticizers when the surfactant employed is predominantly soap.

Hardening Agents

Hardening agents which can increase the hardness or reduce the pliability of the phases are useful optional ingredients especially for the inclusion phase.

Polyols and inorganic electrolytes are useful hardening agents especially when the phase is comprised predominantly of fatty acid soaps. Polyols are defined here as molecules having multiple hydroxyl groups. Preferred polyols include glycerol, propylene glycol, sorbitol, various other sugars and polysaccharides, and polyvinyl alcohol.

In addition to increasing hardness, polyols can also be used to increase the translucency of the phase to allow greater visual contrast.

Preferred inorganic electrolytes include monovalent chloride salts, especially sodium chloride; monovalent and divalent sulfate salts like sodium sulfate; sodium carbonate; monovalent aluminate salts, monovalent phosphates, phosphonates, polyphosphate salts; and mixtures thereof. Further, the bar composition of the invention may include 0 to 25% by weight of crystalline or amorphous aluminum hydroxide. The said aluminum hydroxide can be generated in-situ by reacting fatty acids and/or non-fatty mono- or polycarboxylic acids with sodium aluminate, or can be prepared separately by reacting fatty acids and/or non-fatty mono- or polycarboxylic acids with sodium aluminate and adding the reaction product to the soap.

Another class of hardening agents are insoluble inorganic or mineral solids that can structure the phase by network formation or space-filling. These include fumed, precipitated or modified silica, alumina, calcium carbonate, kaolin, and talc. Alumino-silicate clays especially synthetic or natural hectorites can also be used.

Adjuvants

A wide variety of optional ingredients can be incorporated in one or more of the phases that comprise the bar composition. Examples of adjuvants that can alter the sensory properties, physical properties or chemical stability include but are not limited to: perfumes; pearlizing and opacifying agents such as higher fatty acids and alcohols, ethoxylated fatty acids, solid esters, nacreous "interference pigments" such as $TiO_2$ coated micas; dyes and pigments; sensates such as menthol and ginger; preservatives such as dimethyloldimethylhydantoin (Glydant XL1000), parabens, sorbic acid and the like; anti-oxidants such as, for example, butylated hydroxytoluene (BHT); chelating agents such as salts of ethylene diamine tetra acetic acid (EDTA) and trisodium tetradronate; emulsion stabilizers; auxiliary thickeners; buffering agents; and mixtures thereof.

Skin Benefit Agents

A particular class of optional ingredients highlighted here is skin benefit agents included to promote skin and hair health and condition. Potential benefit agents include but are not limited to: lipids such as cholesterol, ceramides, and pseudoceramides; humectants and hydrophilic skin conditioning agents such as glycerol, sorbitol, propylene glycol, and polyalkalene oxides polymers and resins; antimicrobial agents such as TRICLOSAN; sunscreens such as cinnamates; exfoliant particles such as polyethylene beads, walnut shells, apricot seeds, flower petals and seeds, and inorganics such as silica, and pumice; additional emollients (skin softening agents) such as long chain alcohols and waxes like lanolin; additional moisturizers; skin-toning agents; skin nutrients such as vitamins like Vitamin C, D and E and essential oils like bergamot, citrus unshiu, calamus, and the like; water soluble or insoluble extracts of avocado, grape, grape seed, myrrh, cucumber, watercress, calendula, elder flower, geranium, linden blossom, amaranth, seaweed, gingko, ginseng, carrot; impatiens balsamina, camu camu, alpina leaf and other plant extracts, and mixtures thereof.

The composition can also include a variety of other active ingredients that provide additional skin (including scalp) benefits. Examples include anti-acne agents such as salicylic and resorcinol; sulfur-containing D and L amino acids and their derivatives and salts, particularly their N-acetyl derivatives; anti-wrinkle, anti-skin atrophy and skin-repair actives such as vitamins (e.g., A, E and K), vitamin alkyl esters, minerals, magnesium, calcium, copper, zinc and other metallic components; retinoic acid and esters and derivatives such as retinal and retinol, vitamin B3 compounds, alpha hydroxy acids, beta hydroxy acids, e.g. salicylic acid and derivatives thereof; skin soothing agents such as aloe vera, jahoba oil, propionic and acetic acid derivatives, fenamic acid derivatives; artificial tanning agents such as dihydroxyacetone; tyrosine; tyrosine esters such as ethyl tyrosinate and glucose tyrosinate; skin lightening agents such as aloe extract and niacinamide, alpha-glyceryl-L-ascorbic acid, aminotyroxine, ammonium lactate, glycolic acid, hydroquinone, 4 hydroxyanisole, sebum stimulation agents such as bryonolic acid, dehydroepiandrosterone (DHEA) and orizano; sebum inhibitors such as aluminum hydroxy chloride, corticosteroids, dehydroacetic acid and its salts, dichlorophenyl imidazoldioxolan (available from Elubiol); anti-oxidant effects, protease inhibition; skin tightening agents such as terpolymers of vinylpyrrolidone, (meth) acrylic acid and a hydrophobic monomer comprised of long chain alkyl (meth)acrylates; anti-itch agents such as hydrocortisone, methdilizine and trimeprazine hair growth inhibition; 5-alpha reductase inhibitors; agents that enhance desquamation; anti-glycation agents; anti-dandruff agents such as zinc pyridinethione; hair growth promoters such as finasteride, minoxidil, vitamin D analogues and retinoic acid and mixtures thereof.

Bar Manufacturing Process

The process of the invention is suitable to the efficient production of personal washing bars, e.g., toilet soaps, at moderate to high rates of production (about 50 to about 300 bars per minute; equivalent in mass to about 4.5 to about 27 Kg/min for a 90 gm bar) in an automated fashion. However, the process can also be practiced to make hand crafted bars at lower production rates (<10 bars per minute).

The first step in the process is the production of a billet of extruded cleansing base. The billet is a compacted mass making up the continuous phase of the cleansing article (e.g., toilet soap) and is generally in the form of an ingot having a square or rectangular cross section. The billet is generally formed by passing the continuous phase mass through a single stage or multistage extruder fitted with single or twin screws into a nose cone to compact the mass and finally through an eye plate having a sharply defined opening that provides the appropriate cross sectional dimensions.

The cleansing base can be produced in a standard toilet soap finishing line using processing techniques and equipment well known in the art.

Generally this process involves mixing noodles or flakes of a surfactant mixture dried to the appropriate moisture content with the additional optional ingredients (e.g., perfume color, plasticizing agents) utilizing a batch mixer such a "z-blade" mixer. The objective of this operation is to generate a uniform distribution of the additional ingredients throughout the bulk of the solid surfactant mixture until uniform coating of the noodles or flakes has occurred.

After mixing, the soap mass is generally passed through a refiner followed by a roll mill, e.g., 3-roll mill, to achieve micro-mixing and improve composition uniformity.

The same basic steps of blending, refining and milling are also used to separately prepare the inclusion mass. For continuous process, duplicate sets of mixers, refiners and mills are employed with each set appropriately matched to the volumes and throughputs required for each of the two phases.

Figure 2:
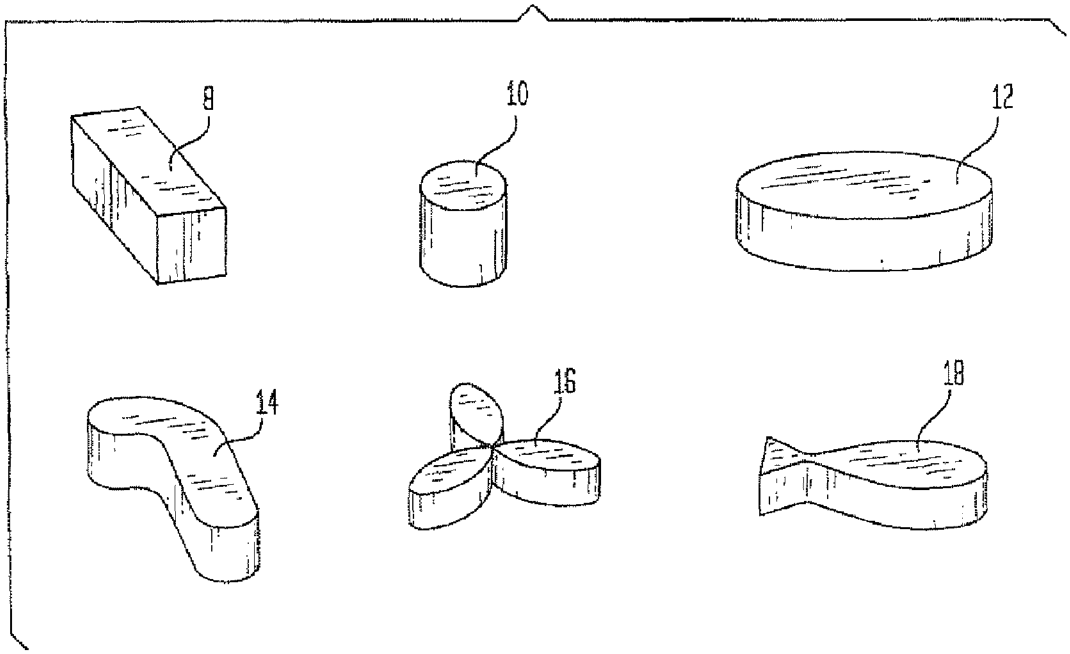
FIG. 2. Illustrates examples of inclusions of various shapes that can be employed in the process.

With reference to FIG. 1, after the phases are prepared, the next step in the process is the placement of the inclusion mass 2 on the surface of the billet 22 of extruded cleansing base 4 to form an inclusion bearing billet 6. The inclusion mass 2 is depicted in FIG. 1 as prismatic particles but in practice these particles can have any of a variety of shapes. With reference to FIG. 2, some of these shapes include but are not limited to: regular geometric forms such as parallelepipeds 8, cylinders 10 or elliptical slices 12; irregular shapes e.g., 14, or iconic shapes such as flower petals 16, or capsules 18. It is preferable that the surface of the inclusion mass particle that contacts the surface of the billet 20 is planar and smooth to enhance traction and stability of the particle on the surface of the billet 22.

A variety of means can be employed to accomplish the placement of the inclusion mass depicted in FIG. 1. Although the inclusion mass can be placed by hand, it is preferable that the placement is carried out in an automated fashion. This can be accomplished with the aide of a robotic arm fitted with a particle grabbing or capture means. Such devices are designed to reproducibly pick up one or several inclusion mass particles from a tray, or conveyor belt and set them on the surface of either a stationary or moving billet in a precise pattern or location or a random pattern having a prescribed dimensional tolerance, e.g., no two inclusions spaced less than 2 mm apart.

Alternatively a conveyor system can be employed in the placement step wherein the inclusion masses in the correct orientation for placement is conveyed to the surface of the billet (stationary or moving) whereupon the inclusion masses are mechanically brought into contact with the surface of the billet and released.

Since the inclusion bearing billet must generally be moved to a stamping machine to accomplish the next phase of the process (see below), the inclusion mass is generally subject to some vibration and mechanical disturbance which can shift its position on the surface of the billet. Furthermore, the stamping process may require a change in the gross orientation of the inclusion bearing billet. The tilt angle, defined as the angular displacement of the surface of the billet from horizontal may then introduce movement of the inclusion phase particles once the frictional force is exceeded. In the extreme, inclusion mass or masses may in fact fall off the extruded billet. Because of these factors, e.g., vibration and tilting, it is desirable to include steps designed to increase the traction or adhesion of the inclusion mass to the billet surface. Several ways to increase inclusion mass to billet adhesion are discussed below.

The joining surfaces (those surfaces that ultimately come into contact) of the billet and/or the inclusion mass can be warmed. This can be accomplished after these masses are fabricated by the use of warm air blown on their surfaces or a heat source such a hot wire or flame brought into close proximity with the surface. Alternatively the eye plate used to shape the billet can be heated on one edge to momentarily raise the temperature of the joining surface on the billet.

An alternative method of increasing adhesion is to apply a material, i.e., a liquid, which promotes adhesion to either of the joining surfaces. This liquid could be water or an aqueous solution or a suitable water soluble organic solvent such ethanol, or a mixture of such liquids. However, this method of promoting adhesion is less preferred because liquid adhesion promoters can migrate outside the interface between the inclusion mass and the billet. Unless the migrated liquid is effectively removed or restricted it can interfere with the subsequent stamping process (see below) by promoting sticking to the dies.

Another means of promoting adhesion which can be used alone or in conjunction with the above technology is the application of a joining force to the inclusion mass during its placement on the billet surface which is sufficient to weld or at least partially adhere the inclusion mass either to the billet, e.g., when this surface has been warmed, or with the film of adhesion promoter if this is employed.

Regardless of the means employed to promote adhesion, it is desirable that the adhesion between the inclusion mass and the billet be sufficiently strong to resist substantial movement of the inclusion mass within a time frame of about 3 sec when the billet is subjected to a tilt angle of 45°, preferably at a tilt angle of 90°, i.e., when the billet is rotated 90° and most preferably at a tilt angle of 180°, i.e., when the billet is turned upside down.

The inclusion bearing billet formed in the process described above is then stamped (molded) utilizing for example a conventional toilet soap stamping apparatus which generally comprising split dies. The stamping process both embeds the inclusion mass into the bar and molds the inclusion bearing billets to the desired final shape. The dies when in the closed position form a mold of defined shape and volume. It is preferable to use capacity dies to form the finished personal washing bars of the invention. These dies compress a billet having a larger volume than the volume capacity of the mold (the space or cavity defined by the dies when they are brought into contact) thus ensuring that the soap is squeezed into all parts of the mold. The excess soap is exuded out of the mold from the edges of the mold. This excess soap commonly known as "lashing" is then removed from the outer edge surfaces of dies and generally recycled (see FIG. 3 items 24—note that for simplicity only the flashing squeezed out from the sides of the mold is shown).

Figure 3A:
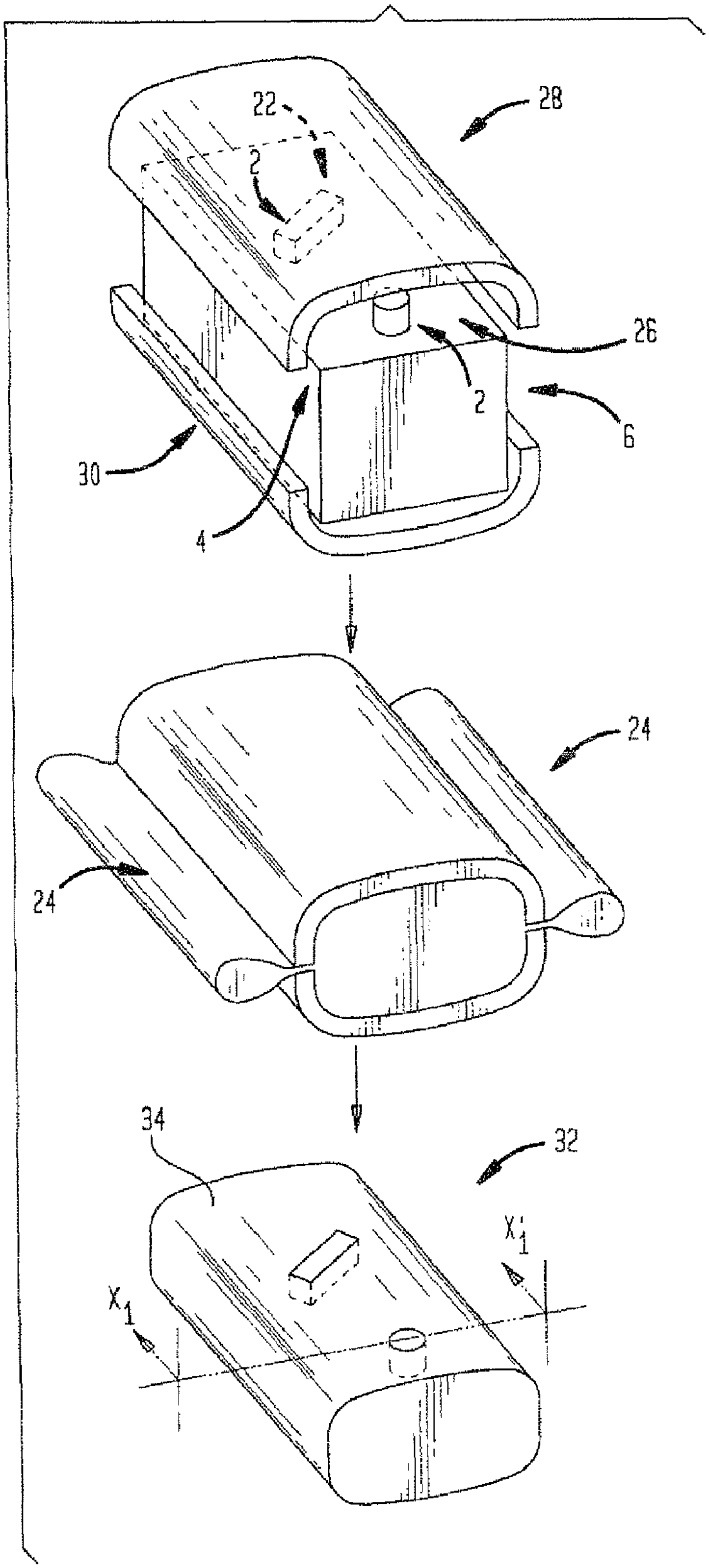
FIG. 3. Perspective view illustrating the stamping steps of the process
Figure 3B:
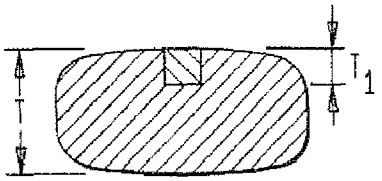

The process of stamping the inclusion bearing billet is shown schematically in a simplified form in FIG. 3. When the inclusion bearing billet 6 is compressed by dies 28 (top die—top half of mold) and 30 (bottom die—bottom half of mold) in a direction perpendicular to the surface of the billet 22, the inclusion bearing billet 6 is squeezed and deforms to fill the mold. Since initially the force of the upper die is concentrated in at the surfaces of the inclusion masses 2, these masses penetrate into the continuous phase mass of the billet. Although there is some lateral spreading of the inclusion mass 2, the majority of the deformation surprisingly occurs in the continuous mass as long as the hardness of the inclusion mass is not very much less than the hardness of the inclusion mass. When the top of the inclusion mass (the face adjacent to the top die) becomes level with the surface of the continuous phase of the billet 22, the entire mass spreads out to fill the mold formed by the closing dies. Excess material (normally 10% to 25% of the mass of material in the mold) is squeezed from the mold during this process and becomes flashing 24.

The flashing is generally recycled. It is desirable in the practice of the invention to ensure that the flashing includes a minimum of the inclusion mass so that its recycle does not lead to a change in appearance of the continuous phase of the bar, e.g., changes in color or clarity. In one embodiment, this can be achieved by careful positioning of the inclusion mass on the billets of the continuous phase during the placement step. The inclusion mass is preferably positioned on the surface of the billet such that the flashing contains less than about 10% of the inclusion mass by weight, more preferably less than about 5%, more preferably less than about 1% and most preferably none of the inclusion mass.

For some applications it is also desirably that the inclusion mass does not substantially spread out or deform during the stamping process. It has been found that lateral deformation of the inclusion mass is minimized when the ratio of the penetrometer hardness of inclusion mass to the penetrometer hardness of the continuous phase is at least about 1.1, preferably at least about 1.15, and most preferably at least about a 1.2 when measured by the Cylinder Impaction Test at the same temperature, i.e., the hardness of the continuous phase and the inclusion mass are measured at the same temperatures and the ratio determined. Ideally the temperature selected is the weight average temperature of the masses at the moment of extrusion (weight of continuous phase times its temperature+weight of all exclusion masses per bar times their temperature divided by the total weight of bar)

When the finished personal washing bar 32 is demolded, the inclusions are clearly visible at the surface of the bar 34 and have well defined and controllable shapes. The inclusions are located in a region of the continuous phase adjacent to the surface of the bar with at least a portion of its outer surface exposed at the surface of the bar. The depth of penetration $T_1$ is essentially controlled by the thickness of the original inclusion mass particle. When the depth of penetration is about 30-50% of the maximum thickener of the bar it remains visible throughout the lifetime of use. However, sometimes it is preferable that this depth of penetration is less than about 50% of the maximum thickness of the bar T, i.e., $T_1/T \div 100$ is less than about 50%, more preferably less than about 40% and most preferably less than about 20% of the maximum thickness of the bar, and still more preferably between about 2% and about 15% of the maximum thickness of the bar.

A significant advantage provided by the process described above is that the inclusions are not substantially overlaid by the continuous phase at the surface and are thus not hidden when the bar is freshly made, i.e., after stamping. Process steps which introduce flows that can obscure the inclusions at the surface of the bar should thus be avoided. By not substantially overlaid by the continuous phase is meant that the fraction of the area of the surface inclusion exposed at the surface of the bar immediately after stamping is at least about 60%, preferably at least about 70% and more preferably at least about 80% relative to the maximum geometric area of the surface inclusion when viewed in any plane parallel to the surface plane of the inclusion (i.e., relative to cross-sectional slices in the inclusion taken at different depths in the bar).

Another advantage of the process described herein is that a strong bond is formed between the inclusion phase and the surrounding continuous extruded soap phase. This bonding produces inclusions that are mechanically robust during use and remain integrated with the continuous phase: a problems encountered in previous methods of forming surface inclusion, especially those employing press-fit inclusions into pre-existing cavities.

Microscopic examination of cross-sections through the bars made with a microtome both perpendicular and parallel to the junction between the phases (side and bottom surfaces) indicates that the junction zone is substantially free from air gaps and defects. By junction zone is meant the region where the two phases abut. By substantially free of defects is meant that less than about 25% of the area of the junction zone, preferably less than 15% and most preferable less than 10% of the area is occupied by gaps or pockets where the phase do not come into actual direct contact.

In contrast, it is observed that the junction zone of multiphase bar made by pressing a soap mass into a preexisting cavity, for example described in WO 99/76355, can contain substantial and multiple defects and air gaps. These gaps provide a site for water accumulation, erosion and debonding that can eventually lead to the fracture and loss of inclusions as the bar is used.

Without wishing to be bound by theory, applicants believe that defect free junction zones are produced by the instant process because the phases which are still in a viscous deformable state are subjected to substantial compressive forces at the junction zone which allows the masses to adhere and removes defects.

Test Methodology

Bar Hardness

A variety of methods are known in the art to measure the hardness of soft solids such as toilet soaps. The techniques used herein is the Cylinder Impaction Test measures the maximum force before yielding. Although the invention is described by parameters that are measured by the Cylinder Impaction Test, various hardness tests such as penetrometers, micro indenters or cheese wires can be used and inter-correlated with the methods used herein.

Cylinder Impaction Test for Hardness

The hardness of the continuous and dispersed phase was measured on extruded and compacted samples using the Cylinder Impaction Test employing a modified Crush-Test protocol that is used for measuring carton strength. A Regmed Crush Tester was employed.

Samples (typically 8×5×2 cm) at the desired temperature were placed on the lower plate of the tester fitted with a pressure gauge and a temperature probe inserted in the sample approximately 4 cm from the test area. An 89 gm inox metallic cylinder (2.2 cm in diameter (0.784 in) and 3 cm in length (1.18 in)) was placed at a central location on the top of the sample. The upper plate was then lowered to just touch cylinder.

The top plate was then lowered at a programmed rate of 0.635±0.13 mm/s (0.025±0.005 in/s). At a certain strain, the sample will yield, bend or fracture and the maximum force expressed as PSI (lbs/inch$^2$) and average sample temperature are recorded. The water content of the sample was measured immediately after the test by microwave analysis. The hardness measurement was repeated a total of 3 times with fresh samples and an average taken. It is important to control the temperature and water content of the sample since hardness is sensitive to both these variables.

Wear Rate—Controlled Rubbing Test

The intrinsic wear rate of the mass e.g., individual phases or finished bar is measured by the following procedure:

a) Place 4 weighed tablets of each test batches on soap trays that have been coded as follows:

| With drainers? | Wash temperature (° C.) |
|---|---|
| Yes | 25 |
| Yes | 40 |
| No | 25 |
| No | 40 |

b) Pour 10 ml distilled water (ambient temperature) into the undrained tray (25° C. and 40° C.).

c) Carry out washdowns on each tablet of soap as follows:
   - Fill washing bowl with about 5 liters of water, at the desired temperature (20° C. or 40° C.).
   - Mark the tablet to identify top face (e.g. make small hole with a needle).
   - Wearing waterproof gloves, immerse the tablet in the water, and twist 15 times (180° each time) in the hands above water.
   - Repeat the above step
   - Briefly immerse tablet in the water to remove lather.
   - Place tablet back on its soap tray, ensuring that the opposite face is uppermost (i.e. the unmarked face).

d) Carry out the full washdown procedure 6 times per day for 4 consecutive days, at evenly spaced intervals during each day (e.g. 9.00, 10.00, 11.00, 13.00, 14.00, 15.00). Alternate the face placed down after each washdown.

e) Between washdowns the soap trays should be left on an open bench or draining board, in ambient conditions. After each washdown cycle, change the position of each soap tray/tablet, to minimise variability in to drying conditions.

f) At the end of each day:
   - rinse and dry each soap tray with drainer
   - drain and refill the soap tray without drainer (24° C. and 40° C.) with 10 ml distilled water (ambient temperature). Consider water hardness of the country.

g) After the last washdown (i.e. Thursday afternoon) rinse and dry all soap trays, and place each tablet on its soap tray.

h) On the 5th day afternoon, turn the samples so that both sides of the tablet dry.

i) On the 8th day, weigh each tablet.

The rate of wear is defined as the weight loss in grams or percentage.

$$\text{Wear} = \frac{(\text{initial weight} - \text{final weight}) * 100\%}{\text{initial weight}} = \text{Result in percentage}$$

$$\text{Wear} = \frac{(\text{initial weight} - \text{final weight})}{\text{initial weight}} = \text{Result in grams}$$

Soap Transparency Test

The degree of transparency was measured using a light transmission tester model EVT 150 manufactured by DMS—Instrumentacao Cientifica Ltd. The instrument consists of a light source providing a 1.5 cm circular beam, a detector fitted to an analog meter, and a sample holder. The measurement procedure is as follows.

The instrument is first set to 100% transmission in air (i.e., without a test sample). The test sample of the bar material, approximately 90 g, having a thickness of 3 cm is placed in the sample chamber and the % transmission relative to air is measured. Normal opaque soap bars have 0% transmission, while translucent bars have a transmission ranging from about 5 to about 40%. Highly transparent bars such as those made by melt-cast processes have a transmission generally greater than 45%.

It has been found that discontinuous phase compositions having a % transmission difference relative to the continuous phase of greater than about 5% are perceived as visually distinctive. Preferably, the difference in light transmission between the phases should be greater than 10%.

EXAMPLES

The following non-limiting examples illustrate various aspects of the invention and preferred embodiments.

Example 1

The composition of the continuous phase used to prepare the bars of example 1 is shown in Table 1. The hardness of this composition as measured by the Cylinder Impaction Test is 30 lb/in$^2$ measured at a temperature of 38° C.,

TABLE 1A

Compositions of continuous phase used in Example 1

| INGREDIENTS | Wt % |
|---|---|
| Sodium soap, Anhydrous (85/15 Tallow/Coco) | 83.0 |
| Preservative | 0.04 |
| Coconut Fatty Acids | 1.0 |
| Glycerol | 0.2 |
| Sodium Chloride | 0.8 |
| Perfume | 1.5 |
| Water | 13.5 |

Billets were formed according to the BAR MANUFACTURING PROCESS described above. In summary, the continuous phase composition was prepared by combining soap noodles (85/15 Tallow/coco soap—sodium salt) with the remaining ingredients in Table 1 in a Z-blade mixer and passing the mixture through a 3-roll mill. (Note that water addition may not be required if sufficient water is present in the soap noodles). The inclusion mass composition was also prepared in a Z-blade mixer.

The composition so processed was added to the hoppers of an extruder and extruded at a temperature of 35° C. at an extrusion rate of 1.5 kg/min through an eyeplate having a 3.5×3.5 cm cross section to form billets cut to about 7 cm in lengths. The eyeplate was not heated.

The compositions used for the inclusion mass are set forth in Table 1B. Both of these compositions yield translucent inclusions.

TABLE 1B

Inclusion compositions used to prepare the bars of Example 2

| INGREDIENT | Ex 1A<br>Wt % | Ex 1B |
|---|---|---|
| Soap (85/15 Tallow/coco) sodium salt | 71 | 70.75 |
| Glycerine | 4 | 9 |
| Propylenoglycol | 1.5 | 1.5 |
| Triethanolamine | 1.5 | 1.5 |
| Sorbitol | 6 | |
| Fatty Acid (C12/14) | 1.25 | 1.25 |
| Water | 13.5 | 13.5 |
| Minors (preservatives pigments, dyes) | 0.25 | 0.5 |
| Perfume | 1 | 1 |

To prepare each inclusion mass, soap noodles were combined with the remaining ingredients (see above note concerning water) listed in Table 1B in a Z-blade mixer. Each mixture was then passed through a 3-roll mill. The compositions were then added to the hopper of a single stage, single screw extruder and extruded at a temperature of 40° C. at an extrusion rate of 0.5 kg/min. The extrudates were passed through an eye plate having multiple openings of a square cross section of about 0.8 cm on edge. The extrudate passing through these openings was cut by a revolving knife to form prismatic bodies roughly 1-2 cm in length (thickness). The inclusion mass is stored at 25° C. in a sealed tray and allowed to temper (e.g., overnight).

About 3-5 inclusions were placed on the surface of the billet described above. The inclusion bearing billets were then carefully transferred to a manual soap stamper and stamped to form the finished personal washing bars utilizing a die set defining a mold having a volume of approximately 88 cm$^3$. The inclusion mass particles were positioned so that after stamping the flashing arising from the molding process did not contain any of the inclusion mass. This required only very limited experimentation and was readily accomplished by defining a zone or area at the perimeter of the billet which had to be left free of inclusion mass particles in order that they did not exude from the mold.

Each bar produced by the above process had readily apparent translucent surface inclusion that had sharp boundaries and exhibited little smearing. In contrast to bars incorporating the same inclusions but formed by incorporating the same inclusions mass during the final extrusion of the continuous phase by for example, the methods of U.S. Pat. No. 6,730,642 had on average less of the inclusions visible at the surface of the bar. Furthermore, these inclusions tended to smear out so that their full geometrical form was obscured.

Example 2

The composition of the continuous phase is set forth the in Table 2A. This composition contains the combination of sunflower seed oil and silicone which act as plasticizers

TABLE 2A

| Compositions of continuous phase used in Example 2 | |
|---|---|
| INGREDIENTS | Wt % |
| Sodium soap, Anhydrous (85/15 Tallow/Coco) | 83.0 |
| Preservative | 0.04 |
| Coconut Fatty Acids | 1.0 |
| Glycerol | 2 |
| Sunflower seed oil | 2 |
| Silicone oil | 2 |
| Sodium Chloride | 0.8 |
| Perfume | 1.5 |
| Water | 13.5 |

The compositions of the inclusion masses are the same as used in Example 1 as identified in Table 2B. Both inclusion masses are translucent.

TABLE 2B

| Inclusion compositions used to prepare the bars of Example 2 | | |
|---|---|---|
| | Ex 2A | Ex 2B |
| Inclusion Phase Composition | Ex 1A Table 1B | Ex 1B Table 1B |

Bars having surface inclusions were prepared by the manual stamping method used in Example 1. Again, the placement of the inclusion mass was chosen such that the flashing exuded from the mold during stamping only contains the continuous phase mass. The inclusions are clearly visible at the surface of the bar with distinct boundaries and very little if any smearing or blurring of the boundaries in contrast to bars made from the same composition but including the inclusion mass during the final extrusion step.

Example 3 and Comparatives C1-C3

The composition of the continuous phase used to make Example Ex3A and Ex3B and comparatives C1-C3 are recorded in Table 3.

TABLE 3

| Continuous phase compositions of Example 3/Comparatives C1–C2 | | | | | |
|---|---|---|---|---|---|
| INGREDIENT | C1 | C2 | C3<br>WT % | Ex 3A | Ex 3B |
| Sodium Soap (Coco fatty acid) | 33.0 | | | | |
| Sodium lauryl sulfate | 7.0 | | | | |
| Anhydrous sodium soap (85% tallow/15% coco) | | To 100% | To 100% | To 100% | To 100% |
| Isopropyl palmitate | | | | 2.0 | |
| Isopropyl myristate | | 5.0 | 3.0 | | 0.5 |
| Dimethicone (5000 cs) | | | | | 0.5 |
| Palm kernel oil fatty acid | | | | | |
| Glycerol | | 0.18 | 0.18 | 0.18 | 0.18 |
| Propylene glycol | 8 | | | | |
| Isopropyl alcohol | 2.5 | | | | |
| Poly ethylene glycol | 5.0 | | | | |
| Sorbitol | 17.5 | | | | |
| MINORS (perfume, colorant, antioxidant, etc) | 2.6 | | | | |
| WATER | TO 100% | 13.5 | 13.5 | 13.5 | 13.5 |
| Hardness (lbs/in$^2$) by Cylinder | <<20 | <<20 | <20 | >20 | >20 |
| Impaction test in temperature range 38° C. to 42° C. | 2 @ 48° C. | 14 @ 32° C. | 20 lbs @ 33.4° C. | 24 @ 38° C. | 28 @ 40.9° C. |

None of the comparative examples C1-C3 are completely suitable for making extruded and stamped bars at high throughput in automated equipment according to the processes disclosed herein.

Composition C1 which is representative of melt-cast (also known as melt and pour) was too soft to extrude and actually liquefied in the plodder.

Composition C2 sticks to the extruder screw and is not transported effectively to the exit of the extruder (i.e., the composition is churned in the extruder).

Composition C3 is marginal. The composition is somewhat sticky but can be extruded at low rates <700 cm$^3$/min. During stamping the composition sticks to the dies and does not unmold cleanly which leads to bars having surface defects.

In contrast both exemplary compositions Ex 3A and Ex 3B are expected to capable of being extruded and stamped at rates somewhere between 50 and about 300 bars/min.

Example 4

This example illustrates the use of a heated eyeplate and the application of a joining force to induce adhesion of the inclusion mass to the surface of the continuous phase billet. The continuous phase and inclusion mass compositions are the same as those used in Ex 1A (see Table 1A and Table 1B). The procedure to prepare bars with surface inclusions is the same as used in Example 1A except for three important modifications.

The upper edge of the eye plate is heated to a temperature of approximately 55° C.

The billets are cut with a cutter and are transferred to a conveyer

The conveyer is paused momentarily while 4 inclusion mass particles are placed on the pre-warmed billet surface. A Teflon® coated plate is placed on the top surface of the inclusion mass particles and a uniform force of about 10 lbs/in$^2$ is applied to the top surface of the plate for about 2-5 seconds. This process step is expected to be sufficient to sinter (weld or fuse) the inclusion mass to the surface of the billet.

The above procedure is anticipated to be sufficient to allow the billets to be turned upside down (rotated to a tilt angle of 180°) without the inclusions falling off for a time period of at least 3 sec. even with gentle tapping of the bottom surface of the billet.

Four inclusion bearing billets are transferred from the conveyor belt to an automated stamping machine via a commercial automated billet handling system. The commercial stamping machine employs dies that are orientated at a 45° angle to the horizontal. The dies are chilled to a temperature of about −10 to −6° C. After stamping the bars are expected to be readily released from the mold and have a similar appearance to the bars produced in examples Ex 1A or Ex 1B.

In contrast, it is not possible to consistently make bars of the same quality using the same process equipment but without utilizing the modifications described above (heated eye plate and application of sufficient pressure to the surface of the inclusion to induce welding) because the inclusions shift and many will fall out of the mold before stamping.

Other techniques can be employed to make the surface of the billet adhesive (e.g., spray-on of liquid, application of heat via flame) and to apply a sufficient joining force (e.g., spring, cam or air driven tappets (rods that "tap" the surface of the inclusions with a controlled force)) so as to induce inclusion-to-billet welding. These techniques can be combined with inclusion handling to achieve a continuous automated process.

Example 5

This example illustrates several optical texture and pattern modifiers that can be used in the inclusion phase. The continuous phase is the same as described in Example Ex 2A and Ex 2B (see Table 2A). The discontinuous phases and appearance modifiers used in Examples Ex 5A to Ex 5E are described in Table 4. Bars are prepared by the methods set forth in Example 1.

The appearance of bars having the above inclusion masses is described in the last row of Table 5. All bars have an artisan-crafted appearance with visually distinctive inclusions that have well defined boundaries at the surface. These exemplary bars provide different textures that can be used to convey to consumers different sensory expectations.

TABLE 4

Inclusion Phases of Example 5

| | Discontinuous phases | | | | |
|---|---|---|---|---|---|
| | EX 5A | EX 5B | EX 5C Wt % | EX 5D | EX 5E |
| INGREDIENTS | | | | | |
| Sodium soap, Anhydrous | Up to 100 | Up to 100 | Up to 100 | Up to 100 | Up to 100 |
| EDTA | 0.02 | 0.02 | 0.02 | 0.02 | 0.02 |
| EHDP | 0.02 | 0.02 | 0.02 | 0.02 | 0.02 |
| Coconut Fatty Acids | 0.5 | 1.25 | 1.25 | 0.5 | 0.5 |
| Sodium Chloride | | 1.26 | 1.26 | | |
| Perfume | 1.50 | 1.55 | 1.55 | 1.50 | 1.50 |
| Water | 17.5 | 13.5 | 13.5 | 17.5 | 17.5 |
| APPEARANCE MODIFIERS | | | | | |
| $TiO_2$ | 0.2 | | | | |
| Speakles[a] | — | — | 1.0 | 1.0 | — |
| Mica[b] | | — | — | 0.3 | 0.3 |
| Glycerol | 6.0 | 9.02 | 9.02 | 8.0 | 8.0 |
| Propylene glycol | | 1.5 | 1.5 | | |
| Triethanolamine | | 1.5 | 1.5 | | |
| Appearance of surface inclusions | Opaque white | Translucent | Translucent with distinctive speckles | Opaque pearlized with distinctive speckles | Opaque pearlized |

[a]Speckles - agglomerated bentonite granules

[b]Mica - Timiron ® and/or Mercare ® Interference Pigment

Example 6

This example illustrates bars having surface inclusions of different shapes. The continuous phase and inclusion mass are the same as employed in Example Ex 1B (see Tables 1A and 1B). The procedure used to manufacture these bars is similar to that described in Example 1 except that different amounts of inclusion phase particles are employed with the different geometries.

The different inclusions mass particles are made by extruding the inclusion mass (composition Ex 1B-Table 1 B) through eye plates having openings of different shapes and cutting the extrudate with a rotating blade. The inclusions are placed on billets in an orientation perpendicular to the direction of extrusion of the inclusion mass so that the shape of the exposed inclusion corresponds to the cross section of the extruded inclusion mass. The shapes of the inclusions are described in Table 5.

TABLE 5

| Description of inclusion phase geometries | | | | |
|---|---|---|---|---|
| | Example | | | |
| | Ex 5A | Ex 5B | Ex 5C | Ex 5D |
| Cross sectional shape of inclusion | Square | Tear drop | 4 petal flower | Mixture Triangle and Square |
| Size of exposed surface | 5 × 5 mm | 7 × 16 mm | 17 mm (end to end) | Triangle 5 mm edge Square 5 mm side |
| Number of Inclusions per billet | 4 | 3 | 1 | 2 + 3 |

The bars after stamping have well defined surface inclusions. Although there is some spreading of the inclusions during stamping, their geometries are easily recognizable and differentiated.

Example 7

This example illustrates the importance of controlling the difference between the intrinsic wear rates of the continuous phase mass and the inclusion mass in the bars of the invention on the in-use sensory properties of the bar.

Bars having the compositions shown in Table 6 were prepared according to the methods set forth in Example 1.

TABLE 6

| Compositions of Example 7 | | | | |
|---|---|---|---|---|
| | Ex 7A | | EX 7B | |
| INGREDIENT | Continuous phase Wt % | Inclusions | Continuous phase | Inclusions |
| Sodium soap anhydrous 85/15 tallow/coco | 83 | 70.95 | | 70.95 |
| Sodium soap anhydrous 40/60 tallow/coco | | | 82.9 | |
| Preservative | 0.04 | | | |
| Coconut fatty acid | 1.0 | 1.25 | 3.5 | 0.5 |
| Glycerol | 0.2 | 9 | 8 | 9 |
| Sodium chloride | 0.8 | 0.8 | | 0.8 |
| Perfume | 1.5 | 1 | 1.28 | 1 |
| Propylene glycol | | 1.5 | | 1.5 |
| Triethanolamine | | 1.5 | | 1.5 |
| Minors | | 0.5 | 0.6 | 0.5 |
| Water | 13.5 | 13.5 | 16 | 8 |

The intrinsic wear rates of the phases that are employed to make the bar of Ex 7A are matched within about 10% of each other as measured by the Controlled Rubbing Test set forth in the TEST METHODOLOGY section. In contrast, the continuous phase employed in Ex 7B has a 25% higher intrinsic wear rate than the inclusion phase and thus the wear rates are mismatched.

The two bars are evaluated in normal use. The Ex 7A bar wears away uniformly with the continuous phase and the inclusions remaining substantially coplanar until the inclusion was eventually exhausted.

In contrast the continuous phase of the Ex 7B bar wear away more quickly than the inclusion phase leaving the inclusion phase as visible exposed lumps rising well above the average surface defined by the continuous phase. The in-use sensory feel of this bar is not unpleasant and could be used to provide a noticeable massaging experience to consumers. However, the composition is perceived as a specialty massage soap and is less preferred as a normal toilet soap designed for everyday use.

Thus, by manipulating the wear rate difference between the phases different product positioning can be supported.

The wear rates can also be manipulated by the inclusion of hardening and plasticizing agents as has been described above.

Example 8

This example illustrates a bar having a continuous phase containing a soap-syndet cleansing base. The composition of the continuous and inclusion phase is shown in Table 7. Bars having prismatic inclusions are made by following the steps described in Examples 1 and 2 with the compositions of Table 7.

TABLE 7

| Compositions for bars of Example 8 | | |
|---|---|---|
| INGREDIENT | Inclusions Wt % | Continuous phase |
| Sodium Soap Anhydrous 85/15 Tallow/Coco | 70.75 | 70 |
| Sunflower oil | | 2 |
| Glycerine | 9 | |
| Propylenoglycol | 1.5 | |
| Triethanolamine | 1.5 | |
| Sorbitol | | |
| Free Fatty Acid (C12-C14) | 1.25 | 0.5 |
| Sodium cocoyl isethionate/Stearic acid blend | | 15 |
| Water | 13.5 | 11 |
| Minors (preservatives pigments, dyes) | 0.5 | 0.5 |
| Perfume | 1 | 1 |

The invention claimed is:

1. A process for the manufacture of an artisan cleansing bar having inclusions embedded in its surface, said process comprising the steps of:

i) forming a billet having a continuous and smooth surface comprised of an extruded cleansing base, ii) placing one or more inclusion masses on the continuous and smooth surface of the billet so as to form an inclusion bearing billet, iii) stamping the inclusion bearing billet in a direction perpendicular to the surface on which the inclusion mass is placed so as to embed the inclusion mass or masses into a surface layer of the billet so as to form a personal washing bar having one or more visually distinct surface inclusions substantially continuous with the continuous phase at the surface of the bar, wherein the extruded cleansing base has a hardness as measured by the Cylinder Impaction Test of at least about 20 lb/in$^2$ when measured at a temperature in the range from about 30° C. to about 42° C.

2. The process according to claim 1 wherein the inclusion mass comprises surfactant.

3. The process according to claim 1 wherein the area of the inclusion mass visually exposed at the surface of the bar immediately after stamping is at least about 60% of the maximum geometric area of the inclusion mass in any plane parallel to the surface of the bar.

4. The process according to claim 1 wherein the extruded cleansing base has a hardness as measured by the Cylinder Impaction Test of at least about 28 lb/in$^2$ when measured at a temperature selected in the range from about 33° C. to about 42° C.

5. The process according to claim 1 wherein the ratio of the hardness of inclusion mass to the hardness of the continuous phase measured at the average temperature of the two masses when they are stamped is at least about 1.1 when measured by the Cylinder Impaction Test.

6. The process according to claim 1 further including the step of applying a means for increasing the adhesion between the extruded billet and inclusion mass such that the inclusion mass adheres to the extruded billet for at least 3 seconds when the inclusion bearing billet is tilted and held at an angle of 90° C. from the horizontal.

7. The process according to claim 6 wherein the means for increasing adhesion is selected from the group consisting of warming the joining surface of either or both the billet and inclusion mass; applying an adhesion promoter to the joining surface of either or both the billet and inclusion mass; applying a joining pressure after the inclusion mass is placed on the surface of the billet, or a combination thereof.

8. The process according to claim 1 wherein the stamping is accomplished by means of dies which when joined forms a mold.

9. The process according to claim 1 wherein none of the inclusion mass exudes from the mold during stamping.

10. The process according to claim 1 wherein the visually distinct surface inclusions have an amorphous shape, a geometric shape, an iconic shape or a combination thereof.

11. The process according to claim 1 wherein the surface inclusion is embedded to a depth of less than 30% of the thickness of the bar.

* * * * *